United States Patent [19]
Provancal et al.

[11] Patent Number: 5,939,057
[45] Date of Patent: Aug. 17, 1999

[54] METHOD OF MAKING POLYHYDRIC ALCOHOL SOLUTIONS OF ENHANCED EFFICACY ANTIPERSPIRANT ACTIVES

[76] Inventors: Stephen J. Provancal, 407 Fairview Ave., Elmhurst, Ill. 60126; Angel L. Carrillo, 11 Vane St., Wellesley, Mass. 02181; Thomas J. Fluhler, 25448 N. Nancy Ct., Hawthorn Woods, Ill. 60047; Richard Oryszczak, 555 N. Williams Dr., Palatine, Ill. 60067; Jayant N. Sane, 32 Pamela Rd., Framingham, Mass. 02879

[21] Appl. No.: 08/874,232

[22] Filed: Jun. 13, 1997

Related U.S. Application Data

[63] Continuation of application No. 08/397,451, Mar. 2, 1995, Pat. No. 5,643,558, which is a continuation-in-part of application No. 08/333,896, Nov. 2, 1994, abandoned.

[51] Int. Cl.[6] ................................ A61K 7/34; A61K 7/38
[52] U.S. Cl. ................................................. 424/66; 424/68
[58] Field of Search .................................. 424/66, 68, 65

[56] References Cited

U.S. PATENT DOCUMENTS

| 3,359,169 | 12/1967 | Slater et al. | 167/90 |
|---|---|---|---|
| 3,405,153 | 10/1968 | Jones et al. | 260/429.3 |
| 3,420,932 | 1/1969 | Jones et al. | 424/47 |
| 3,523,130 | 8/1970 | Jones et al. | 260/448 |
| 3,947,556 | 3/1976 | Jones et al. | 423/463 |
| 3,981,986 | 9/1976 | Rubino | 424/47 |
| 4,781,917 | 11/1988 | Luebbe et al. | 424/65 |
| 5,234,677 | 8/1993 | Murray et al. | 424/68 |
| 5,463,098 | 10/1995 | Giovanniello et al. | 424/66 |

FOREIGN PATENT DOCUMENTS

| 7191 | 1/1980 | European Pat. Off. . |
|---|---|---|
| 295070 | 12/1988 | European Pat. Off. . |
| 404533 | 12/1990 | European Pat. Off. . |

Primary Examiner—Evelyn Huang
Attorney, Agent, or Firm—Stephan P. Williams

[57] ABSTRACT

The present invention comprises a process of preparing a solution of an enhanced efficacy aluminum antiperspirant salt in a polyhydric alcohol by (a) providing an aqueous solution consisting essentially of about 5% to about 18% by weight of an enhanced efficacy aluminum antiperspirant salt in water, the enhanced efficacy aluminum antiperspirant salt having been prepared in situ without having been dried to a solid powder;
(b) mixing the aqueous solution with a sufficient amount of a liquid polyhydric alcohol to provide a mixed solution which has an antiperspirant salt to polyhydric alcohol ratio of about 1:4 to about 1.2:1; and
(c) rapidly evaporating the water from the mixed solution under vacuum to provide a final liquid polyhydric alcohol solution containing about 20 to 50% enhanced efficacy aluminum antiperspirant salt and about 2 to 16% water, with the balance being polyhydric alcohol.

An alkaline glycinate salt, such as sodium, potassium or zinc glycinate, may be added to the polyhydric alcohol prior to the addition of the antiperspirant salt solution in order to raise the pH of the recovered product to about 4.1 to 5.0.

20 Claims, No Drawings

METHOD OF MAKING POLYHYDRIC ALCOHOL SOLUTIONS OF ENHANCED EFFICACY ANTIPERSPIRANT ACTIVES

CROSS-REFERENCE TO RELATED APPLICATION

This application is a continuation of Ser. No. 08/397,451 filed Mar. 2, 1995, now U.S. Pat. No. 5,643,558, which is a continuation-in-part of application Ser. No. 08/333,896 filed Nov. 2, 1994, now abandoned.

FIELD OF THE INVENTION

This invention relates to solutions of enhanced efficacy aluminum antiperspirant actives in polyhydric alcohols.

BACKGROUND OF THE INVENTION

Enhanced efficacy aluminum and aluminum-zirconium antiperspirant salts are well known and are described, for example, in GB 2,048,229, EP 405,598, U.S. Pat. No. 4,359,456, U.S. Pat. No. 4,775,528, U.S. Pat. No. 4,859,446, U.S. Pat. No. 4,871,525, U.S. Pat. No. 4,900,534, U.S. Pat. No. 4,944,933, U.S. Pat. No. 5,202,115, U.S. Pat. No. 5,234,677, U.S. Pat. No. 5,296,623, and U.S. Pat. No. 5,330,751. These enhanced salts are also known to rapidly revert back to their non-enhanced state (for example, as evidenced by an HPLC peak 4 to peak 3 area ratio of 0.3 or less) in solution, particularly at concentrations greater than 20%. Consequently, the enhanced antiperspirant salts are generally only available in powder form.

A number of references describe various ways of making alcohol soluble antiperspirant actives. These references include, for example, U.S. Pat. No. 3,405,153, U.S. Pat. No. 3,420,932, U.S. Pat. No. 3,523,130, and U.S. Pat. No. 3,947,556. In each case concentrated solutions of the antiperspirant active (i.e., in the 40 to 50% range) are employed as a starting material and the product is obtained as a powder, which must then be redissolved in the desired alcohol solution. Such techniques pre-date the availability of enhanced efficacy salts and are not believed to be applicable thereto as they would likely cause reversion to the non-enhanced state. In EP 7191 there is exemplified a process for making a spray dried, powdered complex of enhanced aluminum chlorohydrate and propylene glycol, which complex may then be dissolved in alcohol.

Two methods of making polyhydric alcohol solutions of antiperspirant salts are described in EP 295,070 and EP 404,533. In these methods a powdered antiperspirant salt, which may be an enhanced efficacy salt, is dissolved directly in a polyhydric alcohol, such as propylene glycol. In the former case, the polyhydric alcohol contains about 10 to 20% water. In the latter case, the antiperspirant salt has a water content greater than 10%.

A method of making polyhydric alcohol solutions of antiperspirant salts which are free of unbound water is described in U.S. Pat. No. 4,781,917. In that method, a powdered antiperspirant salt, which may be an enhanced efficacy salt, is dissolved in water (a 50% solution is exemplified), a polyhydric alcohol, such as propylene glycol, is added to the aqueous solution, then all of the water is removed by heating under vacuum. In EP 599,775, example 21 describes a method of making a propylene glycol solution of an aluminum-zirconium antiperspirant salt neutralized with zinc glycinate. An aqeous solution of aluminum chlorohydrate is refluxed in the presence of a small amount of propylene glycol, the solution is cooled to 70° C., zirconyl hydroxychloride-gly is added, the solution is cooled to 40° C., then zinc glycinate followed by propylene glycol is added. This solution is then distilled under vacuum to remove water, leaving a 30% by weight solution of antiperspirant active in propylene glycol.

The above-described methods suffer from a number of deficiencies. Firstly, many of them are not efficient because they utilize a powdered material. Isolation of a powdered antiperspirant salt from solution is time consuming and costly. Secondly, it is believed that these methods will likely result in some loss of efficacy and/or will not provide clear solutions. Antiperspirant salts which have been obtained by spray drying are notoriously difficult to redissolve as clear solutions. Moreover, any method which requires an aqueous salt concentration over 20% will likely suffer some loss in efficacy.

An object of the present invention is to provide an efficient method for the direct preparation of polyhydric alcohol solutions of enhanced efficacy antiperspirant salts without the need to first isolate the salt as a powder and without any significant loss in efficacy. Such solutions may then be used directly in the preparation of antiperspirant compositions.

SUMMARY OF THE INVENTION

The present invention comprises a process of preparing a solution of an enhanced efficacy aluminum antiperspirant salt in a polyhydric alcohol by (a) providing an aqueous solution consisting essentially of about 5% to about 20% by weight of an enhanced efficacy aluminum antiperspirant salt in water, the enhanced efficacy aluminum antiperspirant salt having been prepared in situ without having been dried to a solid powder;

(b) mixing the aqueous solution with a sufficient amount of a liquid polyhydric alcohol to provide a mixed solution which has an antiperspirant salt to polyhydric alcohol ratio of about 1:4 to about 1.2:1; and (c) rapidly evaporating the water from the mixed solution under vacuum to provide a liquid polyhydric alcohol solution containing about 20 to 50% enhanced efficacy aluminum antiperspirant salt and about 2 to 16% water, with the balance being said polyhydric alcohol.

An alkaline glycinate salt, such as sodium or zinc glycinate, may be added to the polyhydric alcohol prior to the addition of the antiperspirant salt solution in order to raise the pH of the recovered product to about 4.1 to 5.0.

DETAILED DESCRIPTION OF THE INVENTION

The first step in the process of the present invention, i.e. step (a), requires the preparation of an aqueous solution consisting essentially of about 5% to about 20%, preferably about 8% to about 15%, by weight of an enhanced efficacy aluminum antiperspirant salt in water, the enhanced efficacy aluminum antiperspirant salt having been prepared in situ without having been dried to a solid powder.

Any of the known methods of preparing aqueous solutions of enhanced efficacy antiperspirant salts may be utilized. These methods include those described, for example, in GB 2,048,229, EP 405,598, U.S. Pat. No. 4,359,456, U.S. Pat. No. 4,775,528, U.S. Pat. No. 4,859,446, U.S. Pat. No. 4,871,525, U.S. Pat. No. 4,900,534, U.S. Pat. 4,944,933, U.S. Pat. No. 5,202,115, U.S. Pat. No. 5,234,677, U.S. Pat. No. 5,296,623, and U.S. Pat. No. 5,330,751. Irrespective of the method of preparation utilized, it is critical that the enhanced efficacy salts, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. The term "enhanced efficacy aluminum antiperspirant salt" is intended to mean a salt which produces such an HPLC chromatogram.

The preferred aluminum antiperspirant salts are any of the conventional aluminum salts and aluminum-zirconium salts known to be useful in antiperspirant compositions. These salts include aluminum hydroxy halides (e.g., aluminum chlorohydrate), and mixtures or complexes thereof with zirconyl oxyhalides and zirconyl hydroxyhalides (e.g. aluminum-zirconium chlorohydrate).

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 8, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 8 and a metal: Cl ratio of about 0.9 to 2.1. Such complexes may also contain a neutral amino acid, preferably glycine, typically with a Zr:Gly ratio of about 1:1 to 1:4.

A preferred method of preparing aqueous solutions of enhanced efficacy antiperspirant salts comprises heating a 5 to 18% aqueous solution of aluminum salt, preferably aluminum chlorohydrate, at a sufficient temperature and for a sufficient time to provide an HPLC peak 4 to peak 3 area ratio of at least 0.5, preferably at least 0.7, and most preferably at least 0.9, with at least 70% of the aluminum contained in said peaks. The aqueous solution may be obtained by diluting a standard commercially available 50% salt solution with water to the desired concentration, which is preferably 8 to 15%. The temperature and time of heating may be adjusted as necessary to achieve the desired degree of conversion to the enhanced state. Generally, longer times are required at lower temperatures. It is preferred to heat above 50° C., more preferably at 70° to 100° C., for at least two hours, more preferably for at least 10 hours or more. Excellent results are obtained by heating at about 80° to 85° C. for about 15 to 20 hours.

An alternative method of preparing aqueous solutions of enhanced efficacy aluminum hydroxy halides is that described in U.S. Pat. No. 4,859,446 and U.S. Pat. No. 5,356,609, the disclosures of which are incorporated herein by reference. In this method aluminum metal is reacted with aluminum halide, typically aluminum chloride, or with hydrogen halide, typically hydrochloric acid, in water at a temperature of about 50° to 100° C., the concentration of the reactants being such as to provide an aqueous solution of aluminum hydroxy halide, typically aluminum chlorohydrate, of about 8 to 25%, preferably about 10 to about 20%, by weight.

If the antiperspirant salt utilized in step (a) is an aluminum-zirconium salt, it is preferred to prepare this salt by following one of the above-described methods for making the aqueous solution of enhanced aluminum salt, then adding the zirconium salt, preferably zirconyl hydroxychloride, usually in the form of an aqueous solution, to the enhanced aluminum salt solution in an amount to provide an Al:Zr ratio of about 1.7 to about 12.5, preferably about 2 to about 8. Naturally, the amount of each salt should be adjusted so that the final solution will have a total salt concentration within the limits specified as desired for step (a). It is also possible to add the zirconium salt to the aluminum salt solution prior to the above-described heating step which converts the aluminum to the enhanced state.

The liquid polyhydric alcohol which is utilized in step (b) may be selected from any of those which are generally used in cosmetic compositions and which are liquid at room temperature. These typically include liquid aliphatic alcohols having from 2 to 12 carbon atoms and two or more hydroxyl groups and liquid polyaliphatic ether-polyhydroxy compounds. These include, for example, propylene glycol (either 1,2- or 1,3-), butylene glycol, diethylene glycol, dipropylene glycol, glycerin, sorbitol, trimethylol propane, 2-methyl-2,4-pentane-diol, 2-ethyl-1,3-hexane-diol, polyethylene glycols, polypropylene glycols and mixtures thereof. The preferred liquid polyhydric alcohols are propylene glycol, butylene glycol, diethylene glycol, dipropylene glycol, glycerin, sorbitol and mixtures thereof. Most preferred are propylene glycol and sorbitol.

The liquid polyhydric alcohol may be mixed with the aqueous antiperspirant salt solution at any temperature between about 0° C. and about 100° C., preferably between room temperature and 85° C. The amount of polyhydric alcohol (or conversely, the amount of antiperspirant salt solution) should be that amount which will provide, after the evaporation step (c), the desired concentration of antiperspirant salt in the polyhydric alcohol solution which is recovered. Generally, it is preferred to utilize an amount of polyhydric alcohol in step (b) that will provide a mixed solution which has an antiperspirant salt to polyhydric alcohol weight ratio of about 1:4 to about 1.2:1, preferably about 1:3 to about 1:1.

After the addition of the liquid polyhydric alcohol, the mixed solution is subjected to evaporation conditions in step (c) in order to remove most, but not all, of the water so as to provide a liquid polyhydric alcohol solution containing about 20 to 50%, preferably about 30 to 47%, enhanced efficacy antiperspirant salt and about 2 to 16%, preferably about 4 to 12%, water, with the balance being said polyhydric alcohol. The evaporation step should be conducted under such conditions that the enhanced efficacy state of the antiperspirant salt, as evidenced by HPLC peak 4 to peak 3 area ratio, is substantially retained. Thus, it is generally important that the salt not be exposed to high temperature conditions for any significant length of time. Accordingly, the evaporation step is preferably conducted under vacuum, typically under 150 mm Hg (absolute pressure), preferably about 5 to about 70 mm Hg (absolute pressure), and at temperatures under 110° C., preferably about 20° to about 85° C.

While the evaporation step may be conducted in any suitable type of vacuum evaporation equipment, the use of a rotary vacuum evaporator or a flash vacuum evaporator is especially preferred. To minimize the extent of reversion of the enhanced salt to non-enhanced form during the evaporation step, it is important to complete the conversion of a given aliquot of mixed solution (i.e. the solution prior to evaporation) to the recovered polyhydric alcohol solution in the shortest possible time. When relatively large amounts of material (i.e. amounts of 100 liters or more) are to be subjected to evaporation, it is preferred to conduct the evaporation in a continuous manner such as, for example, by continuously feeding portions of mixed solution to the inlet of a vacuum evaporator and withdrawing the desired polyhydric alcohol solution from the outlet of the evaporator. In this way it is possible to complete the conversion of a given aliquot of solution in under four hours. Preferably, the average residence time of antiperspirant salt in the evaporator should be about three hours or less. The skilled worker should have no difficulty selecting appropriate equipment to carry out the rapid evaporation as described.

It is also possible to conduct the afore-described process with several variations. In one variation, the aqueous salt solution provided in step (a) may be concentrated (for example, in a vacuum evaporator) to about 40 to 50% salt concentration prior to adding the polyhydric alcohol solution in step (b). If zirconium salt is to be added, it may be added either before or preferably after this concentration step. If this procedure is followed, it is most important that steps (b) and (c) are carried out as rapidly as possible so as to avoid any deterioration in peak 4 to peak 3 ratio. This is because the higher concentration salt solution is much more prone to reversion to the non-enhanced state.

In another variation, it is possible to add an aqueous zirconium salt solution in an amount to provide the requisite Al:Zr ratio either (i) to the mixed solution after the liquid polyhydric alcohol has been added in accordance with step (b) or (ii) to the liquid polyhydric alcohol before it is added in accordance with step (b). Thus, when an aluminum-zirconium complex is desired in the final product, the zirconium salt can be added at any stage prior to the evaporation step (c).

It is preferred that the polyhydric alcohol solution of enhanced efficacy antiperspirant salt which is recovered in the process of the present invention will retain substantially the same degree of enhanced efficacy in the salt as was there when the salt was prepared. That is, the enhanced efficacy salt, when reconstituted as a 10% aqueous solution, should produce an HPLC chromatogram (as described, for example, in U.S. Pat. No. 5,330,751) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. The 10% aqueous salt solution which is subjected to chromatographic analysis may be prepared either by diluting the polyhydric alcohol solution with sufficient water to form a 10% aqueous salt solution or by precipitating the salt from the polyhydric alcohol by addition of acetone, then redissolving the salt in water at a concentration of 10%.

The method of the present invention is particularly advantageous for the preparation of polyhydric alcohol solutions of enhanced efficacy aluminum-zirconium antiperspirant salts, preferably aluminum-zirconium chlorohydrate salts, containing higher levels of glycinate salts, such as sodium or zinc glycinate, which increases the pH of the antiperspirant. That is, the pH of the recovered solution (when measured after addition of an equal part of distilled water) will fall within the range of about 4.1 to 5.0, preferably about 4.4 to 5.0, when a sufficient amount of additional alkaline glycinate salt is added during the process, typically an amount sufficient to bring the total Gly:Zr ratio to about 1.3 or higher, preferably about 1.5:1 to about 4:1, more preferably about 1.5:1 to about 3:1. By alkaline glycinate salt is meant any metal glycinate salt which is soluble in polyhydric alcohol and water and which partially neutralizes the acidity of the antiperspirant salt without otherwise causing any reduction in clarity of the final product. Preferred alkaline glycinates are sodium, potassium and zinc glycinate.

To make antiperspirant solutions of higher glycine content in accordance with the present invention, the order of addition of the various components is critical in order to avoid salt precipitation. First, an aqueous solution of alkaline glycinate, such as 50% sodium glycinate, is added to the polyhydric alcohol, typically propylene glycol, prior to addition of the antiperspirant salt components. To this solution is added an aqueous solution of zirconium hydroxychloride glycinate (typically a 50% solution with Gly:Zr ratio about 1:1). Then an aqueous solution of enhanced efficacy aluminum chlorohydrate (typically 10% ACH') is added. This solution is then subjected to vacuum evaporation as previously described to remove most of the water, providing a polyhydric alcohol solution containing about 20 to 50% by weight aluminum-zirconium chlorohydrate glycinate (Gly:Zr ratio of about 1.5:1 to 4:1), and 2 to 16% water, with a pH between about 4.1 and 5.0 when diluted with an equal portion of water. It should be noted that reference throughout this application to weight percent of antiperspirant salt is intended to be calculated as weight percent of the salt including glycine or glycinate in accordance with conventional industry standards.

EXAMPLE 1

An aqueous 50% aluminum chlorohydrate (ACH) solution was diluted with water to form a 10% ACH solution and this solution was heated at about 80° C. for about 16 to 17 hours to form the enhanced efficacy salt solution (ACH'). To 1350 g of this 10% ACH' solution was added 185 g zirconium hydroxychloride glycinate (50% aqueous ZHC.gly solution). To this solution was added 271 g propylene glycol and the combined solution was evaporated in a Buchi RE-111 rotary vacuum evaporator at about 140 mm Hg (beginning) to 20 mm Hg (end) (absolute pressure) and about 60–72° C. (residence time about 3.5 to 4 hours) to provide a clear solution comprising 44.8% propylene glycol, 46.7% enhanced efficacy aluminum-zirconium-tetrachlorohydrex-glycine (more than 80% of aluminum in peaks 3 and 4 with peak 4 to peak 3 area ratio of 1.0), and 8.5% water.

EXAMPLE 2

To 241 lbs. (109.4 kg) 10% ACH' solution (prepared as in Example 1) was added 32 lbs. (14.5 kg) ZHC.gly solution (50%), then 129 lbs. (58.6 kg) propylene glycol. The combined solution was preheated to 70–75° C. and continuously fed at about 3–4 gals/hr into a type JHE flash evaporator (APV Crepaco Inc., Tonawanda, N.Y.; evaporator modified by mounting to the top of the flash chamber a 3 foot rectification tower filled with about 2.5 feet of 0.5 inch ceramic Berl saddles) maintained at about 60 mm Hg (absolute pressure) from which was withdrawn at about 1 gal/hr a clear solution comprising 60.5% propylene glycol, 33.7% enhanced efficacy aluminum-zirconium-tetrachlorohydrex-glycine (more than 80% of aluminum in peaks 3 and 4 with peak 4 to peak 3 area ratio of 1.1), and 5.8% water. The average residence time of an aliquot of solution in the evaporator was about 3 hours.

EXAMPLE 3

To 1640 g of warm 10% ACH' solution (prepared as in Example 1) was added 360 g propylene glycol and the combined solution was evaporated in a Buchi RE-111 rotary vacuum evaporator at about 140 mm Hg (beginning) to 20 mm Hg (end) (absolute pressure) and about 46–72° C. (residence time about 3.5 to 4 hours) to provide a clear solution comprising 62.7% propylene glycol, 30.3% enhanced aluminum chlorohydrate (more than 80% of aluminum in peaks 3 and 4 with peak 4 to peak 3 area ratio of 1.37), and 7.0% water.

EXAMPLE 4

A 50% sodium glycinate solution was prepared by mixing 171 lbs. (77.6 kg) 50% NaOH with 67.8 lbs. (30.8 kg) water, then adding 160.3 lbs (72.8 kg) of glycine (1:1 mole ratio of glycine to NaOH), the temperature rising from 25° to 30° C., then from 30° to 35° C., after the first and second additions respectively. To 103.3 lbs. (46.9 kg) of propylene glycol was added 7.8 lbs. (3.5 kg) of 50% sodium glycinate and the solution mixed for ten minutes. To this solution was added 33.9 lbs. (15.4 kg) of zirconium hydroxychloride glycinate (50% aqueous ZHC.Gly solution, Gly:Zr ratio about 1:1). After mixing this solution for about ten minutes, 255 lbs. (115.8 kg) of 10% ACH' solution (prepared as in Example 1) was added and mixed for about ten minutes. This solution is preheated to about 70° to 75° C. and fed continuously to a type JHE flash evaporator as described in Example 2. A clear solution is obtained comprising 65% propylene glycol, 30% enhanced efficacy aluminum-zirconium-tetrachlorohydrex-glycine (more than 80% of aluminum in peaks 3 and 4 with peak 4 to peak 3 area ratio greater than 1 and Gly:Zr ratio about 1.6:1), and 5% water. The pH of a sample of this solution diluted with an equal portion of distilled water was about 4.7.

What is claimed is:

1. A clear product comprising a clear polyhydric alcohol solution of about 20 to 50% by weight dissolved enhanced efficacy aluminum antiperspirant salt and about 2 to 16% by weight water, wherein said polyhydric alcohol solution is made by a process which comprises
   (a) providing an aqueous solution of an enhanced efficacy aluminum antiperspirant salt, said enhanced efficacy aluminum antiperspirant salt having been prepared in situ without having been dried to a solid powder;
   (b) mixing said aqueous solution with a liquid polyhydric alcohol to provide a mixed solution, the amount of said polyhydric alcohol being sufficient to provide, after the evaporation step (c), the desired concentration of the antiperspirant salt in the polyhydric alcohol solution which is recovered; and
   (c) rapidly evaporating the water from said mixed solution under vacuum to provide said polyhydric alcohol solution.

2. The product of claim 1 wherein step (c) is performed such that the conversion of a given aliquot of mixed solution to polyhydric alcohol solution is completed in less than four hours.

3. The product of claim 2 wherein step (c) is performed at about 5 to about 70 mm Hg (absolute pressure) and about 20° to about 85° C.

4. The product of claim 3 wherein step (c) is performed in a continuous manner by continuously adding said mixed solution to the inlet of a vacuum evaporator and withdrawing said polyhydric alcohol solution from the outlet of said vacuum evaporator.

5. The product of claim 4 wherein wherein the average residence time of antiperspirant salt in the evaporator is about three hours or less.

6. The product of claim 1 wherein the enhanced efficacy aluminum antiperspirant salt is a mixture or complex of $Al_2(OH)_{6-a}X_a$ and $ZrO(OH)_{2-pb}Y_b$ wherein X is Cl, Br, I, or $NO_3$, a is about 0.3 to about 4, Y is Cl, Br, I, $NO_3$ or $SO_4$, b is about 0.8 to about 2, p is the valence of Y, and the Al:Zr ratio is about 1.7 to about 12.5., wherein said salt has an HPLC peak 4 to peak 3 area ratio of at least 0.7 with at least 70% of the aluminum contained in said peaks.

7. The product of claim 6 wherein the polyhydric alcohol is selected from the group consisting of propylene glycol, butylene glycol, diethylene glycol, dipropylene glycol, glycerin, sorbitol and mixtures thereof.

8. The product of claim 7 wherein the enhanced efficacy aluminum antiperspirant salt is aluminum-zirconium chlorohydrate.

9. The product of claim 8 wherein the enhanced efficacy aluminum antiperspirant salt has an HPLC peak 4 to peak 3 area ratio of at least 0.9.

10. The product of claim 1 wherein the enhanced efficacy aluminum antiperspirant salt is $Al_2(OH)_{6-a}X_a$ wherein X is Cl, Br, I, or $NO_3$, and a is about 0.3 to about 4, wherein said salt has an HPLC peak 4 to peak 3 area ratio of at least 0.7 with at least 70% of the aluminum contained in said peaks.

11. The product of claim 10 wherein the polyhydric alcohol is selected from the group consisting of propylene glycol, butylene glycol, diethylene glycol, dipropylene glycol, glycerin, sorbitol and mixtures thereof.

12. The producy of claim 11 wherein the enhanced efficacy aluminum antiperspirant salt is aluminum chlorohydrate.

13. The product of claim 7 additionally comprising a solubilized alkaline glycinate in an amount sufficient to provide a total Gly:Zr ratio in the product of about 1.3:1 to about 4:1.

14. The product of claim 13 wherein said alkaline glycinate is sodium glycinate, potassium glycinate or zinc glycinate.

15. A clear product comprising a clear polyhydric alcohol solution of about 20 to 50% by weight dissolved enhanced efficacy aluminum-zirconium chlorohydrate glycinate having an HPLC peak 4 to peak 3 area ratio of at least 0.7 with at least 70% of the aluminum contained in said peaks, an Al:Zr ratio of about 2 to about 8 and a Gly:Zr ratio of about 1.3:1 to about 4:1, and about 2 to 16% by weight water, wherein said polyhydric alcohol solution is made by a process which comprises
   (a) providing a liquid polyhydric alcohol which contains a solubilized alkaline glycinate, the amount of solubilized alkaline glycinate being sufficient to provide a total Gly:Zr ratio of about 1.3:1 to about 4:1 in the recovered product;
   (b) providing a first aqueous solution consisting essentially of about 40% to about 50% by weight zirconium hydroxychloride glycinate in water;
   (c) providing a second aqueous solution consisting essentially of about 5% to about 20% by weight of an enhanced efficacy aluminum chlorohydrate in water, said enhanced efficacy aluminum chlorohydrate having been prepared in situ without having been dried to a solid powder and having an HPLC peak 4 to peak 3 area ratio of at least 0.7 with at least 70% of the aluminum contained in said peaks;

(d) mixing said first aqueous solution with said liquid polyhydric alcohol to provide a first mixed solution;

(e) mixing said second aqueous solution with said first mixed solution to provide a second mixed solution;

wherein the amount of each of the components (a), (b) and (c) is such as to provide a second mixed solution which has an aluminum-zirconium chlorohydrate to polyhydric alcohol weight ratio of about 1:4 to about 1.2:1 and an Al:Zr ratio of about 2 to about 8; and (f) rapidly evaporating the water from said second mixed solution under vacuum to provide said polyhydric alcohol solution.

16. A clear product comprising a clear polyhydric alcohol solution containing about 2 to 16% by weight water and about 20 to 50% by weight dissolved aluminum-zirconium chlorohydrate glycinate having an HPLC peak 4 to peak 3 area ratio of at least 0.7 with at least 70% of the aluminum contained in said peaks and an Al:Zr ratio of about 2 to about 8.

17. The product of claim 16 comprising about 4 to 12% water.

18. The product of claim 16 having a Gly:Zr ratio of about 1.3:1 to about 4:1.

19. The product of claim 18 having a pH of about 4.1 to 5.0.

20. The product of claim 17 wherein the aluminum-zirconium chlorohydrate glycinate has a peak 4 to peak 3 area ratio of at least 0.9.

* * * * *